(12) United States Patent
Cowles

(10) Patent No.: US 6,451,808 B1
(45) Date of Patent: Sep. 17, 2002

(54) INHIBITION OF EMETIC EFFECT OF METFORMIN WITH 5-HT3 RECEPTOR ANTAGONISTS

(75) Inventor: Verne E. Cowles, Dublin, CA (US)

(73) Assignee: DepoMed, Inc., Menlo Park, CA (US)

( * ) Notice: Subject to any disclaimer, the term of this patent is extended or adjusted under 35 U.S.C. 154(b) by 0 days.

(21) Appl. No.: 09/691,398

(22) Filed: Oct. 17, 2000

(51) Int. Cl.$^7$ .................. A01N 43/42; A61K 31/44
(52) U.S. Cl. .................. 514/290; 514/296; 514/299
(58) Field of Search .................. 424/464; 514/290, 514/296, 299

(56) References Cited

U.S. PATENT DOCUMENTS

| | | | |
|---|---|---|---|
| 4,695,578 A | 9/1987 | Coates et al. | |
| 4,789,673 A | 12/1988 | Donatsch et al. | |
| 5,576,306 A | 11/1996 | Dressman et al. | |
| 5,789,393 A | 8/1998 | Dressman et al. | |
| 5,955,106 A | 9/1999 | Moeckel et al. | |
| 6,031,004 A | 2/2000 | Timmins et al. | |

OTHER PUBLICATIONS

Cubeddu et al., "Effects of metformin on intestinal 5-hydroxytryptamine (5-HT) release and on 5-HT$_3$ receptors," *Arch. Pharmacol.* (2000) 361: 85–91.

*Primary Examiner*—Alton Nathaniel Pryor
(74) *Attorney, Agent, or Firm*—Townsend and Townsend and Crew, LLP

(57) ABSTRACT

Metformin is formulated as a pharmaceutical composition that also includes a 5-hydroxytryptamine-3 receptor antagonist to suppress the gastrointestinal side effects that are associated with metformin administration in many patients.

11 Claims, No Drawings

INHIBITION OF EMETIC EFFECT OF METFORMIN WITH 5-HT3 RECEPTOR ANTAGONISTS

BACKGROUND OF THE INVENTION

1. Field of the Invention

This invention addresses the drug metformin and its possible side effects.

2. Description of the Prior Art

Metformin, or specifically metformin hydrochloride, is an oral antihyperglycemic drug used in the management of non-insulin-dependent (Type II) diabetes. The scientific name of metformin hydrochloride is 1,1-dimethylbiguanide monohydrochloride, and its chemical formula is

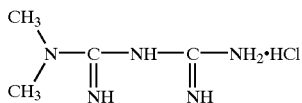

An unfortunate side effect associated with metformin is the occurrence of gastrointestinal reactions such as diarrhea, nausea, vomiting, abdominal bloating, flatulence, and anorexia. These reactions occur with approximately 30% greater frequency when compared to placebo-treated subjects, particularly at the initiation stages of metformin administration. The reactions are dose-related, and methods of controlling these reactions include reducing the dose, escalating the dose gradually, or taking the drug with meals. In severe cases, however, dehydration and prerenal azotemia can occur, and many subjects undergoing metformin therapy are forced to discontinue their use of the drug.

SUMMARY OF THE INVENTION

It has now been discovered that emesis and other gastrointestinal side effects of metformin can be reduced or eliminated by administering a 5-hydroxytryptamine-3 (5-HT$_3$) receptor antagonist in combination with the metformin. With this co-administration, metformin can be administered at higher dosages for many patients without the need to take the drug with meals. The patient can thus apply greater flexibility in the manner and timing by which the drug is taken without concern about the side effects that are unpleasant to both the patient and to those in the presence of the patient. The use of 5-HT$_3$ antagonists in accordance with this invention is particularly useful when administered during the first week or first month of metformin therapy, since nausea is most prevalent during this initial period. The administration of 5-HT$_3$ antagonists improves the ease by which the patient can be "titrated" to an effective level of metformin for controlling blood glucose.

The 5-HT$_3$ antagonists of particular interest are ondansetron, granisetron, dolasetron, and tropiseton, and others that have molecular structures with a similar 1H-indole or 1H-indazole nucleus. The success achieved with this invention however indicates that 5-HT$_3$ antagonists in general will serve the common purpose of controlling these side effects.

DETAILED DESCRIPTION OF THE INVENTION AND PREFERRED EMBODIMENTS

Preferred 5-hydroxytryptamine-3 receptor antagonists for use in this invention are substituted 1H-indoles having the generic formula

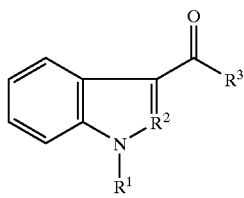

in which R' is a member selected from the group consisting of H and lower alkyl, and either:

R$^2$ and R$^3$ are combined to form a divalent structure having one of the following formulae:

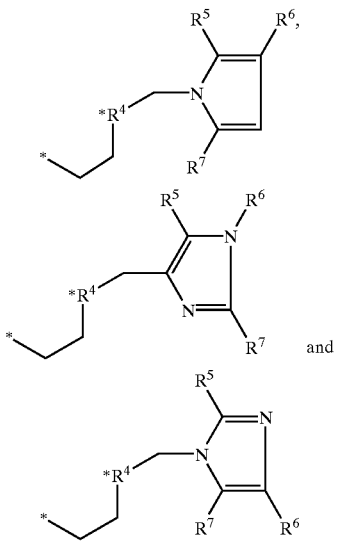

where * denotes sites of attachment, R$^4$ is either N or CH, and R$^5$, R$^6$, and R$^7$ (two or all of which may be the same or all may be different) are either H, lower alkyl, cycloalkyl, or lower alkenyl, or R$^2$ is N or CH, and R$^3$ is

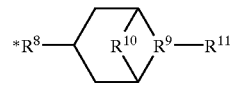

where * again denotes the site of attachment, R$^8$ is NH or O, R$^9$ is N or CH, and either R$^{10}$ is lower divalent alkyl and R$^{11}$ is H or lower alkyl, or R$^{10}$ and R$^{11}$ are combined to form either lower trivalent alkyl or oxo-substituted lower trivalent alkyl.

The terms used in defining the formulas appearing in this specification and claims have the same meanings that they have when used in conventional organic nomenclature. Thus, "alkyl" denotes a saturated hydrocarbyl group, including both unbranched and branched groups. Similarly, "alkenyl" denotes a hydrocarbyl group that is unsaturated due to its inclusion of one or more double bonds, again including both unbranched and branched groups. "Lower alkyl" or "lower alkenyl" denotes an alkyl or alkenyl group of relatively few carbon atoms. The term "oxo-substituted" indicates that one or more carbon atoms bears an oxygen atom in the form of a carbonyl group, —C(=O)—.

Within the scope of the generic formula shown above, certain embodiments are preferred, notably those in which R$^5$, R$^6$, and R$^7$ (two or all of which may be the same or all may be different) are either H or $C_1$–$C_3$ alkyl, $R^9$ is N, and either $R^{10}$ is divalent $C_2$–$C_3$ alkyl and $R^{11}$ is H or $R^{10}$ and $R^{11}$ are combined to form either $C_4$–$C_6$ trivalent alkyl or oxo-substituted $C_4$–$C_6$ trivalent alkyl. The four specific 5-$HT_3$ receptor antagonists mentioned above are all within the scope of the generic formula. The molecular structures of these compounds and other 5-$HT_3$ receptor antagonists within the scope of this invention are as follows:

Ondansetron: 1,2,3,9-Tetrahydro-9-methyl-3-[(2-methyl1-H-imidazole-1-yl)methyl]-4H-carbazol-4-one

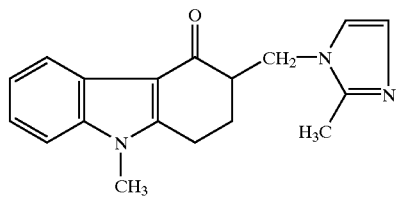

Granisetron: Endo-1-methyl-N-(9-methyl-9-azabicyclo[3.3.1]non-3-yl)-1H-indazole-3-carboxamide

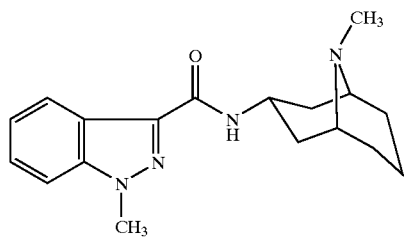

Tropisetron: Endo-1H-indole-3-carbocylic acid8-methyl-8-azabicyclo[3.2.1]oct-3-yl ester

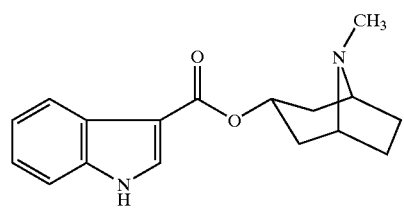

Dolasetron: 1H-Indole-3 -carboxylic acid (2a, 6a, 8a, 9up)-octahydro-3-oxo-2,6-methano-2H-quinolizin-8-yl Ester

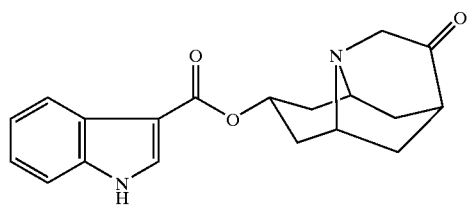

Azasetron: (±)-N-Azabicyclo[2.2.2]oct-3-yl-6-chloro-3,4-dihydro-4-methyl-3-oxo-1,4-benzoxazine-8-carboxamide

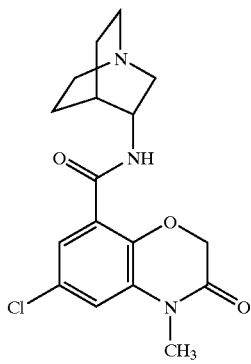

Alosetron: 2,3,4,5-Tetrahydro-5-methyl-2-[(5-methyl-1H-imidazol-4-yl)methyl]-1H-pyrido[4,3-b]indol-1-one

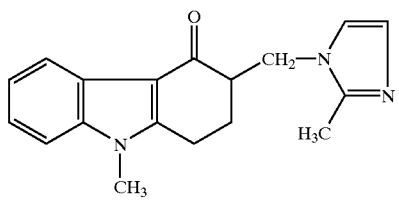

Ramosetron

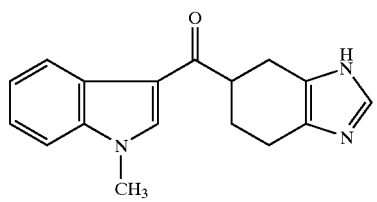

Other 5-$HT_3$ receptor antagonists that can be used in the practice of this invention are hydrodolasetron (an active metabolite of dolasetron), 3-tropanyl-indole-3-carboxylate methiodide, KB-R6933, GK-128, metoclopramide, LY-278, 584, and MDL-72222.

The term "metformin" is used herein to include both metformin and metformin hydrochloride, and any other forms of metformin, including therapeutically active salts, that have similar therapeutic activity. Examples of therapeutically active salts of metformin are disclosed in Timmins et al. (Bristol-Myers Squibb Company), U.S. Pat. No. 6,031, 004, issued Feb. 29, 2000, the disclosure of which is incorporated herein by reference.

The relative amounts of metformin and 5-$HT_3$ receptor antagonist to be administered in accordance with this invention are not critical to the invention and may vary, depending on such factors as the past history of the patient, the general condition of the patient, the particular means of administration, and the type of the dosage form. In most cases, best results will be obtained when the weight ratio of metformin to 5-$HT_3$ receptor antagonist is within the range of from about 1:0.0001 to about 2:1, preferably from about 1:0.0003 to about 0.5:1.

The amount of metformin contained in a single dosage form may likewise vary and is not critical to the invention. The term "pharmaceutically effective amount" as used herein denotes any amount that has a beneficial therapeutic effect on the patient to whom the dosage form is administered. Optimal amounts will vary with the condition of the patient, the type of dosage form, and whether the dosage form is a sustained-release or immediate-release dosage form. In most cases, best results will be achieved with dosage forms that contain from about 100 mg to about 5000 mg of metformin, preferably from about 200 mg to about 2000 mg.

The metformin and 5-HT$_3$ receptor antagonist combination are administered orally in the practice of this invention, and the dosage form may be any form that is suitable for oral administration. While liquid formulations can be used, the preferred formulations are tablets or capsules. The metformin and 5-HT$_3$ receptor antagonist may both be included in a single dosage form (i.e., a single solution, tablet or capsule), or separate dosage forms administered simultaneously or in succession.

The metformin and the 5-HT$_3$ receptor antagonists can be incorporated in the dosage forms in any of various ways. Either or both agents may for example be incorporated in such a manner to cause substantially immediate release into the gastric fluid as soon as the dosage form enters the stomach. Alternatively, either or both agents may be incorporated in such a manner to cause release into the gastric fluid in a sustained manner, such as by dissolution and diffusion out of a solid matrix in which the agent is retained, or by slow erosion of the solid matrix. A still further alternative is a combination whereby a portion of either agent is released immediately and the remainder is released in a sustained manner. A still further alternative, and one that is particularly preferred in the practice of this invention, is one in which the metformin is incorporated in a sustained-release manner while the 5-HT$_3$ receptor antagonist is incorporated in a manner that provides immediate release (or relatively rapid release, such as within a few minutes of ingestion). In preferred embodiments of the invention in general, the metformin is preferably retained in a solid matrix that releases the metformin to the gastric environment in a sustained (i.e., continuous and prolonged) manner.

Solid matrices that provide sustained release for use in this invention may assume any of various forms. One form is a solid mass impregnated with the substance(s) and releasing the substance(s) either by virtue of the fact that the gastric fluid dissolves the substance upon being absorbed by the matrix and then carries the dissolved substance with it as the solution diffuses out of the matrix. Another is a solid mass impregnated with the substance(s), the mass itself being gradually erodible upon contact with gastric fluid and releasing the substance(s) by the process of erosion. A third is an osmotic dispensing device, which is a compartmented enclosure with one compartment containing the substance(s) to be dispensed and another (or part of the same compartment) that has a permeable wall through which gastric fluid enters by osmosis. When the device contains individual compartments, the compartments are separated by a flexible or movable wall, and the entering gastric fluid forces the substance out of the enclosure through a dispensing port. Dispensing of the substance(s) thus occurs by osmotic pressure. Disclosures of osmotic dispensing devices of this general type are found in U.S. Pat. Nos. 3,916,899 (inventors Theeuwes, Felix, et al., issue date Nov. 4, 1975), 5,340,590 (inventors Wong, Patrick S. L., et al., issue date Aug. 23, 1994), and 5,938,654 (inventors Wong, Patrick S. L., et al., issue date Aug. 17, 1999). The disclosures of each of these patents are incorporated herein by reference.

In dosage forms that release the 5-HT$_3$ receptor antagonist, either in whole or in part, substantially immediately into the gastric fluid, this immediate release can be achieved by placing most, and preferably all, of the antagonist outside the matrix that retains the metformin. One way of achieving this is by incorporating the antagonist in a solid layer or solid coating over the metformin-containing matrix. Another way is by adding the antagonist in powdered form to a capsule that also contains the particles of the metformin-containing matrix.

When the 5-HT$_3$ receptor antagonist is contained in a solid layer or coating, the layer or coating preferably consists of the antagonist retained in a matrix that rapidly disintegrates upon contact with the gastric fluid and thereby releases the antagonist into the fluid. Film-forming matrices that can be used include cellulosics, vinyls, glycols, acrylics, and other carbohydrates. Examples of cellulosics are hydroxypropylmethycellulose, hydroxypropylcellulose, hydroxyethylcellulose, carboxymethylcellulose, ethyl cellulose, and microcrystalline cellulose. Examples of vinyls are polyvinylpyrrolidone, crospovidone, and polyvinyl alcohol. Examples of glycols are polyethylene glycols, polyethylene oxides, sodium starch glycolate, and poloxamers. Examples of acrylates are dimethylaminoethylmethacrylate, methacrylic acid copolymers and ethyl acrylate-methyl methacrylate copolymers. Examples of other carbohydrates are maltodextrins, polydextrose, lactose and zein. Sodium starch glycolate and microcrystalline cellulose are particularly preferred.

In certain embodiments of this invention, the dosage form is a water-swellable polymer matrix which is in the form of particles that are small enough for oral administration yet rapidly swell upon imbibition of water from gastric fluid to a size sufficiently large that they are retained in the stomach for several hours during the fed mode. The swollen particles maintain their size long enough to be held in the stomach for the desired duration of drug delivery, which is generally in excess of several hours. The metformin and the 5HT$_3$ receptor antagonist may thus both be retained in a common solid matrix, or they may be retained in separate solid matrices, each forming a distinct layer of a single tablet, or separate tablets. Placement of the two components in separate matrices permits the use of different matrices to achieve different release rates or profiles for each component.

In those embodiments of the invention in which the dosage form is a water-swellable polymer, any polymer that is non-toxic, that swells in a dimensionally unrestricted manner upon imbibition of water, and that provides for sustained release of an incorporated ingredient can be used. Examples of polymers that function in this manner are cellulose polymers and their derivatives (such as for example, hydroxyethylcellulose, hydroxypropylcellulose, carboxymethylcellulose, and microcrystalline cellulose, polysaccharides and their derivatives, polyalkylene oxides, polyethylene glycols, chitosan, poly(vinyl alcohol), polysaccharide gums, maleic anhydride copolymers, poly(vinyl pyrrolidone), starch and starch-based polymers, poly (2-ethyl-2-oxazoline), poly(ethyleneimine), polyurethane hydrogels, and crosslinked polyacrylic acids and their derivatives. Further examples are copolymers of the polymers listed in the preceding sentence, including block copolymers and grafted polymers. Specific examples of copolymers are PLURONIC® and TECTONIC®, which are polyethylene oxide-polypropylene oxide block copolymers available from BASF Corporation, Chemicals Div., Wyandotte, Mich., USA.

The terms "cellulose polymer" and "cellulosic polymer" are used herein to denote linear polymers of anhydroglucose. Preferred cellulosic polymers are alkyl-substituted cellulosic polymers that ultimately dissolve in the gastrointestinal (GI) tract in a predictably delayed manner.

Preferred alkyl-substituted cellulose derivatives are those substituted with alkyl groups of 1 to 3 carbon atoms each. Examples are methylcellulose, hydroxymethylcellulose, hydroxyethylcellulose, hydroxypropylcellulose, hydroxypropylmethylcellulose, and carboxymethylcellulose. In terms of their viscosities, one class of preferred alkyl-substituted celluloses includes those whose viscosity is within the range of about 100 to about 110,000 centipoise as a 2% aqueous solution at 20° C. Another class includes those whose viscosity is within the range of about 1,000 to about 4,000 centipoise as a 1% aqueous solution at 20° C. Particularly preferred alkyl-substituted celluloses are hydroxyethylcellulose and hydroxypropylmethylcellulose. A presently preferred hydroxyethylcellulose is NATRASOL® 250HX NF (National Formulary), available from Aqualon Company, Wilmington, Del., USA.

Polyalkylene oxides of greatest utility in this invention are those having the properties described above for alkyl-substituted cellulose polymers. A particularly preferred polyalkylene oxide is poly(ethylene oxide), which term is used herein to denote a linear polymer of unsubstituted ethylene oxide. For agents having high solubility in water, poly(ethylene oxide) polymers having molecular weights of about 4,000,000 and higher are preferred. More preferred are those with molecular weights within the range of about 4,500,000 to about 10,000,000, and even more preferred are polymers with molecular weights within the range of about 5,000,000 to about 8,000,000. Preferred poly(ethylene oxide)s are those with a weight-average molecular weight within the range of about $1 \times 10^5$ to about $1 \times 10^7$, and preferably within the range of about $9 \times 10^5$ to about $8 \times 10^6$. Poly(ethylene oxide)s are often characterized by their viscosity in solution. For purposes of this invention, a preferred viscosity range is about 50 to about 2,000,000 centipoise for a 2% aqueous solution at 20° C. Two presently preferred poly(ethylene oxide)s are POLYOX® NF, grade WSR Coagulant, molecular weight 5 million, and grade WSR 303, molecular weight 7 million, both products of Union Carbide Chemicals and Plastics Company Inc. of Danbury, Conn., USA. Two other preferred poly(ethylene oxide)s are POLYOX® NF, grade WSR 301, molecular weight 4 million, and grade WSR N60K, molecular weight 2 million, both products of Union Carbide Chemicals and Plastics Company Inc. of Danbury, Conn., USA. For agents of low water solubility, release of the agent from the matrix may be achieved at least in part by erosion of the matrix. Poly(ethylene oxide) matrices can be made more erodible by the inclusion poly(ethylene oxide) of a lower molecular weight (less than 1,000,000). Mixtures of polyethylene oxides of different molecular weights can also be used regardless of the water solubility of the agent.

Polysaccharide gums suitable for use in this invention include both natural and modified (semi-synthetic) polysaccharide gums. Examples are dextran, xanthan gum, gellan gum, welan gum and rhamsan gum. Xanthan gum is preferred.

Crosslinked polyacrylic acids of greatest utility are those whose properties are the same as those described above for alkyl-substituted cellulose and polyalkylene oxide polymers. Preferred crosslinked polyacrylic acids are those with a viscosity ranging from about 4,000 to about 40,000 centipoise for a 1% aqueous solution at 25° C. Three presently preferred examples are CARBOPOL® NF grades 971P, 974P and 934P (BFGoodrich Co., Specialty Polymers and Chemicals Div., Cleveland, Ohio, USA). Further examples are polymers known as WATER LOCK®, which are starch/-acrylates/-acrylamide copolymers available from Grain Processing Corporation, Muscatine, Iowa, USA.

The hydrophilicity and water swellability of these polymers cause the matrices to swell in size in the gastric cavity due to ingress of water in order to achieve a size that will be retained in the stomach when introduced during the fed mode. These qualities also cause the matrices to become slippery, which provides resistance to peristalsis and further promotes their retention in the stomach. The release rate of the metformin from the matrix will be primarily dependent upon the rate of water imbibition and the rate at which the drug dissolves and diffuses from the swollen polymer, which in turn is related to the particle size and the metformin concentration in the matrix. By using polymers that dissolve very slowly in gastric fluid, the matrix will maintain its physical integrity over a substantial period of time, in many cases at least 90% and preferably over 100% of the dosing period. The particles will then slowly dissolve or decompose. Complete dissolution or decomposition may not occur until 24 hours or more after the intended dosing period ceases, although in most cases, complete dissolution or decomposition will occur within 10 to 24 hours after the dosing period. For erodible systems, where the main mechanism of drug release is through dissolution of the polymer, dissolution may occur within 2 to 8 hours.

When a polymeric matrix is used, the metformin is preferably dispersed homogeneously in the polymeric matrix, although effective results can also be achieved with a non-homogeneous distribution. The weight ratio of metformin to polymer is not critical and may vary. In most cases, however, best results will be obtained with a metformin:polymer weight ratio within the range of about 1:9 to about 9:1, preferably about 1:1 to about 9:1, and most preferably about 4:1 to about 9:1.

The particles are preferably consolidated into a packed mass for ingestion, even though they will separate into individual particles once ingested. Conventional methods can be used for consolidating the particles in this manner. For example, the particles can be placed in gelatin capsules known in the art as "hard-filled" capsules and "soft-elastic" capsules. The compositions of these capsules and procedures for forming them are known among those skilled in drug formulations. The encapsulating material should be highly soluble in gastric fluid so that the particles are rapidly dispersed in the stomach after the capsule is ingested.

One presently preferred dosage form is a size 0 gelatin capsule containing either two or three pellets of drug-impregnated polymer. For two-pellet capsules, the pellets are cylindrically shaped, 6 mm in diameter and 10.5 mm in length. For three-pellet capsules, the pellets are again cylindrically shaped, 6 mm in diameter and 7 mm in length. For a size 00 gelatin capsule with two pellets, the pellets are cylindrical, 7.5 mm in diameter and 11.75 mm in length. For a size 00 gelatin capsule with three pellets, the pellets are cylindrical, 7.5 mm in diameter and 4.8 mm in length. These are merely examples; the shapes and sizes can be varied considerably.

The following examples are offered by way of illustration, and are not intended to impose limits on the scope of the invention.

EXAMPLES

Two adult beagle dogs were administered metformin and ondansetron in various combinations and dosages to determine the effects of each in terms of inducing or suppressing nausea and vomiting. The metformin was administered directly to the stomachs of the dogs by way of antral catheters, and the ondansetron was administered intravenously. When both were administered, the metformin dosage was administered fifteen minutes after the ondansetron. Contractions of the smooth muscle of the gastrointestinal tracts of the dogs were monitored with strain gauge force transducers to permit detection of retrograde giant contractions (RGCs). The times at which either RGCs or vomiting occurred were recorded. Vomiting is always preceded by RGCs, while RGCs may also occur without vomiting and are generally thought to be an indication of nausea. The results of the tests are shown in the following table.

TABLE

Test Results

| Dog | Test No. | Ondansetron Dosage (mg/kg) | Metformin Dosage (mg/kg) | Observations |
|---|---|---|---|---|
| A | 1 | none | 25 | RGCs alone occurred at 58 and 78.5 min after metformin administration; RGCs followed by vomiting occurred at 91, 99, 106.5, and 109.5 minutes |
|   | 2 | 0.15 | 25 | one RGC and vomit occurred at 179 minutes after metformin administration |
|   | 3 | 0.15 | 25 | no RGCs or vomiting occurred |
| B | 1 | none | 25 | one RGC occurred at 79 minutes after metformin administration, with no vomiting |
|   | 2 | none | 50 | RGCs and vomiting occurred at 80 and 106 minutes after metformin administration |
|   | 3 | 0.15 | 50 | no RGCs or vomiting occurred |
|   | 4 | 0.15 | 50 | no RGCs or vomiting occurred |

These results demonstrate that ondansetron is effective in suppressing the emetic effects of a metformin dosage.

The foregoing is offered primarily for purposes of illustration. Further variations and modifications of the formulations, dosages, and methods of administration that will still fall within the spirit and scope of the invention will be readily apparent to those skilled in the art.

What is claimed is:

1. A pharmaceutical composition consisting essentially of:
   (i) a pharmaceutically effective amount of metformin;
   (ii) a 5-hydrotryptamine-3 receptor antagonist selected from the group consisting of ondansetron, dolasetron, granisetron, and tropisetron, in an amount effective in suppressing emesis that is otherwise caused by said metformin; and
   (iii) a pharmaceutically acceptable carrier.

2. A pharmaceutical composition in accordance with claim 1 in which said 5-hydroxytryptamine-3 receptor antagonist is a member selected from the group consisting of ondansetron, dolasetron, granisetron, and tropisetron.

3. A pharmaceutical composition in accordance with claim 1 in which said 5-hydroxytryptamine-3 receptor antagonist is ondansetron.

4. A pharmaceutical composition in accordance with claim 1 in which said 5-hydroxytryptamine-3 receptor antagonist is dolasetron.

5. A pharmaceutical composition in accordance with claim 1 in which said 5-hydroxytryptamine-3 receptor antagonist is granisetron.

6. A pharmaceutical composition in accordance with claim 1 in which said 5-hydroxytryptamine-3 receptor antagonist is tropisetron.

7. A pharmaceutical composition in accordance with claim 1 in which said metformin and said 5-hydroxytryptamine-3 receptor antagonist are present in a weight ratio of from about 1:0.0001 to about 2:1.

8. A pharmaceutical composition in accordance with claim 1 in which said metformin and said 5-hydroxytryptamine-3 receptor antagonist are present in a weight ratio of from about 1:0.0003 to about 0.5:1.

9. A pharmaceutical composition in accordance with claim 1 in which said pharmaceutically effective amount of metformin is from about 100 mg to about 5000 mg.

10. A pharmaceutical composition in accordance with claim 1 in which said metformin is retained in said composition in a sustained-release condition and said 5-hydroxytryptamine-3 receptor antagonist is retained in said composition in an immediate-release condition.

11. A pharmaceutical composition in accordance with claim 1 in which said metformin is retained in said composition in a sustained-release tablet and said 5-hydroxytryptamine-3 receptor antagonist is retained in a rapid-release layer on the surface of said tablet.

* * * * *